(12) United States Patent
Chen

(10) Patent No.: US 10,584,311 B2
(45) Date of Patent: Mar. 10, 2020

(54) **METHOD FOR ASEPTICALLY CULTURING FRUITING BODIES OF *ANTRODIA CINNAMOMEA***

(71) Applicant: Shiu-Nan Chen, Taipei (TW)

(72) Inventor: Shiu-Nan Chen, Taipei (TW)

(73) Assignee: Shiu-Nan Chen, Taipei (TW)

( * ) Notice: Subject to any disclaimer, the term of this patent is extended or adjusted under 35 U.S.C. 154(b) by 473 days.

(21) Appl. No.: 15/342,160

(22) Filed: Nov. 3, 2016

(65) Prior Publication Data
US 2017/0295724 A1 Oct. 19, 2017

(30) Foreign Application Priority Data

Apr. 19, 2016 (TW) .............................. 105112108 A

(51) Int. Cl.
*C12N 1/14* (2006.01)
*A01H 15/00* (2006.01)

(52) U.S. Cl.
CPC ...................................... *C12N 1/14* (2013.01)

(58) Field of Classification Search
None
See application file for complete search history.

(56) References Cited

U.S. PATENT DOCUMENTS

| 6,558,943 B1* | 5/2003 | Li | C12N 1/14 424/93.5 |
| 2008/0102512 A1* | 5/2008 | Tsai | A01H 15/00 435/256.8 |
| 2009/0227001 A1* | 9/2009 | Wang | A61K 36/07 435/244 |

FOREIGN PATENT DOCUMENTS

TW  I422680 B  1/2014

OTHER PUBLICATIONS

Cherng et al. "Triterpenoids from Antrodia Cinnamomea" Phytochemistry, vol. 41, No. 1, pp. 263-267, 1996 (Year: 1996).*
Oil Jug, sunflower oil article (Year: 2019).*

* cited by examiner

*Primary Examiner* — Blaine Lankford
*Assistant Examiner* — Lauren K Van Buren
(74) *Attorney, Agent, or Firm* — McCarter & English, LLP; Yu Lu

(57) ABSTRACT

The present disclosure provides a method for aseptically culturing fruiting bodies of *Antrodia cinnamomea*, including: inoculating *Antrodia cinnamomea* strains in a sterilized agar medium, and performing a subculture to generate secondary mycelia and fruiting bodies of *Antrodia cinnamomea*.

11 Claims, 6 Drawing Sheets
(5 of 6 Drawing Sheet(s) Filed in Color)

METHOD FOR ASEPTICALLY CULTURING FRUITING BODIES OF *ANTRODIA CINNAMOMEA*

REFERENCE TO RELATED APPLICATIONS

This application claims foreign priority under 35 U.S.C. § 119(a) to Patent Application No. 105112108, filed on Apr. 19, 2016, in the Intellectual Property Office of Ministry of Economic Affairs, Republic of China (Taiwan, R.O.C.), the entire contents of the above-referenced application is incorporated herein by reference.

BACKGROUND OF THE INVENTION

*Antrodia cinnamomea* is a type of perennial mushroom belonging to *Antrodia* species of *Antrodia* (Polyporaceae, Aphyllophorales). *Antrodia cinnamomea* is a species of wood-decay fungus which only grows on old *Cinnamomum kanehirai* hay in Taiwan. A body of *Antrodia cinnamomea* has a porous surface which is bright red at an initial stage and becomes milky white, reddish brown, brownish or fawn when growing. Fruiting bodies are generated from hollow interior trunks of *Cinnamomum kanehirai* hay or from a bottom of laid deadwoods of *Cinnamomum kanehirai* hay, having a strong scent of *Cinnamomum kanehirai*.

*Antrodia cinnamomea* has been regarded as a valuable fungi medicinal material. In many researches, triterpenoids are found to be one family of the most important ingredients in *Antrodia cinnamomea*, and contents of triterpenoids in *Antrodia cinnamomea* are far more than the one in *Lucid ganoderma*. In addition, other compounds such as physiologically active ingredients including polysaccharides, superoxide dismutase, adenosine, $\beta$-D-glucans, and so on contained therein have a health effect in terms of physiological function of human beings. Triterpenoids have a main function for inhibiting growth of cancer cells, inhibiting release of histamine, preventing allergy, improving hepatic function, promoting platelet aggregation, bringing about a hypolipemic effect, and so on. The more contents and types of triterpenoids are, the higher a medicinal value thereof is. It has been proved from experiments that triterpenoids can inhibit multiplication of hepatoma carcinoma cells. A hypertensive patient often suffers a stroke caused by cerebrovascular rupture due to high blood pressure, and triterpenoids can inhibit activity of Angiotensin Converting Enzyme (ACE) effectively so as to lower down the blood pressure. Furthermore, triterpenoids are effective in anti-inflammation.

Since *Cinnamomum kanehirai* hay has been listed as a national protected species and protected from illegal logging, *Antrodia cinnamomea* is difficult to be collected and is various in qualities. Additionally, natural grown *Antrodia cinnamomea* may contain heavy metal contaminants more or less due to increasingly serious environment pollution. Thus, most of *Antrodia cinnamomea* is cultivated artificially in the recent years. According to Taiwan Patent No. 1422680, conventional artificial cultivation methods include basswood cultivation, solid state cultivation and liquid fermentation.

However, the basswood cultivation cannot be performed in an aseptic environment, and can thus be easily contaminated by other microorganisms. Further, sources of basswoods are not easy to control, and the basswoods can possibly be contaminated. *Antrodia cinnamomea* yielded from the basswood cultivation shows toxicity to adrenal gland in animal experiments and can cause an increase in weights of liver and ovary of a mouse.

The solid state cultivation is performed mainly by culturing *Antrodia cinnamomea* in a growth bag containing nutriments (i.e., a current method for culturing forest mushrooms). Harvested *Antrodia cinnamomea* has an appearance similar to *Antrodia cinnamomea* grown in the wild and/or with the basswood cultivation, but has a low content of triterpenoids. Also, other main ingredients thereof are different from those of fruiting bodies of *Antrodia cinnamomea* grown in the wild and/or with the basswood cultivation.

Furthermore, in terms of the liquid fermentation, a liquid fermentation product of *Antrodia cinnamomea* generally can be harvested in a short time However, a product therefrom contains mainly polysaccharides and no triterpenoids. In addition, other main ingredients of the product greatly differ from those in fruiting bodies of *Antrodia cinnamomea* grown in the wild and/or with the basswood cultivation.

In view of aforementioned facts, a novel method for culturing fruiting bodies of *Antrodia cinnamomea* must be provided to successfully generate fruiting bodies of *Antrodia cinnamomea* in an aseptic environment, and the main ingredients thereof such as triterpenoids therein should be similar to those in the *Antrodia cinnamomea* grown in the wild and/or with the basswood cultivation, thereby bringing about a health effect on human beings.

SUMMARY OF THE INVENTION

The present disclosure provides a method for culturing fruiting bodies of *Antrodia cinnamomea* which includes: inoculating *Antrodia cinnamomea* strains in a sterilized agar medium; performing subculturing to generate secondary mycelia; selecting, during the subculturing, the secondary mycelia with no-mutation and no-toxicity; and subjecting the secondary mycelia with no-mutation and no-toxicity to a further subculturing to generate the fruiting bodies.

The aforementioned agar medium comprises: a yeast malt (YM) agar culture matrix; edible oil in an amount greater than 0% to 1% based on the total weight of the sterilized agar medium; and yeast extract in an amount greater than 3% and less than 5% based on the total weight of the sterilized agar medium. The aforementioned agar medium has water in balance.

The present disclosure further provides a method for culturing fruiting bodies of *Antrodia cinnamomea*, comprising a step of further selecting secondary mycelia with no-mutation and no-toxicity and fruiting bodies after having performed a subculture in the agar medium to generate secondary mycelia with no-mutation and no-toxicity and fruiting bodies, and inoculating the secondary mycelia with no-mutation and no-toxicity and the fruiting bodies in a sterilized solid medium in a container to generate further subcultures of the secondary mycelia with no-mutation and no-toxicity or the fruiting bodies.

The aforementioned sterilized solid medium comprises a solid portion containing at least one type of grain; and a liquid portion containing at least one of a saccharide, yeast extract and edible oil, wherein, based on the total weight of the liquid portion, the saccharide is in an amount of from 3% to 5%, the yeast extract is in an amount of from 3% to 5%, and the edible oil is greater than 0% and less than 1%; and wherein a height of the liquid portion in the container is from semi-high of the solid portion to substantially equal-high as a top surface of the solid portion. The aforementioned solid medium contains water in balance.

The present disclosure further provides a method for culturing fruiting bodies of *Antrodia cinnamomea*, comprising harvesting secondary mycelia with no-mutation and no-toxicity from the agar medium in which a subculture has been performed to generate secondary mycelia with no-mutation and no-toxicity, inoculating the secondary mycelia with no-mutation and no-toxicity in a sterilized liquid medium in a container to generate the fruiting bodies. The liquid medium comprises a saccharide; yeast extract; and edible oil, wherein, based on the total weight of the liquid medium, the saccharide is in an amount of from 3% to 5%, the yeast extract is in an amount of from 3% to 5%, and the edible oil is in an amount greater than 0% and less than 1%.

The present disclosure further provides a method for culturing fruiting bodies of *Antrodia cinnamomea*, including inoculating the secondary mycelia with no-mutation and no-toxicity, which have been cultured in the solid culture, in a sterilized liquid medium in a container to generate the fruiting bodies. The liquid medium comprises a saccharide; yeast extract; and edible oil, wherein, based on the total weight of the liquid medium, the content of the saccharide is greater than 3% and less than 5%, the content of the yeast extract is greater than 3% and less than 5%, and the content of the edible oil is greater than 0% and less than 1%.

The method for aseptically culturing fruiting bodies of *Antrodia cinnamomea* of the present disclosure comprises inoculating *Antrodia cinnamomea* strains in an agar medium in an aseptic environment; performing subculturing to generate secondary mycelia with no-mutation and no-toxicity. As such, culturing the secondary mycelia with no-mutation and no-toxicity directly can yield non-toxic and contamination-free fruiting bodies of *Antrodia cinnamomea* having the same indicative ingredients as those contained in *Antrodia cinnamomea* grown in the wild and/or with the basswood cultivation.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
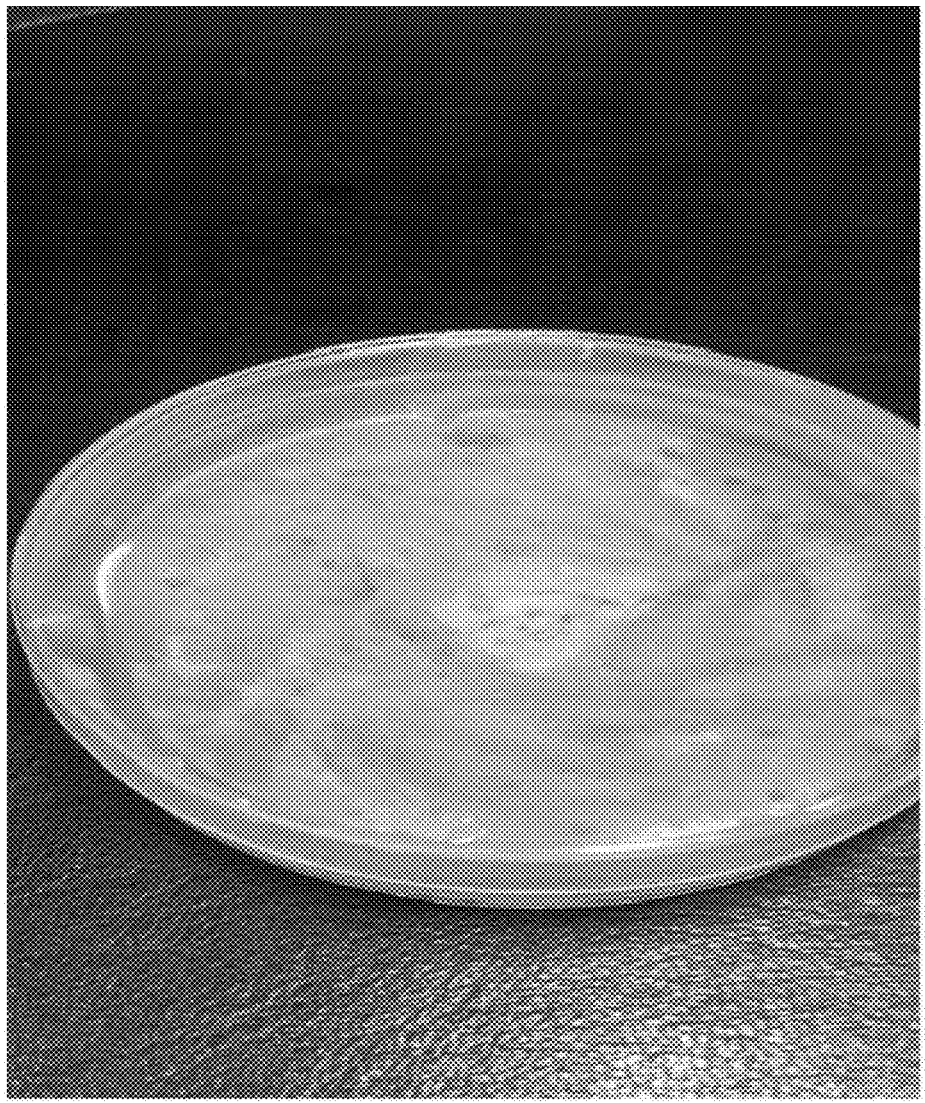
FIG. 1 is a photograph showing fruiting bodies of *Antrodia cinnamomea* obtained from a subculture.

Implementations of the present disclosure will be illustrated by specific embodiments as follows, and a person skilled in the art can readily conceive advantages and effects of the present disclosure based on contents described in the specification. The present disclosure also can be performed or applied to other different examples. Also, detailed description in the present specification can be differently modified and altered based on different views and applications without departing from the spirits described in the present disclosure.

A term "Matrix" used herein indicates one occupying more than 50% of a total weight. In general, mycelia hyphae containing a single nucleus and growing from strains of fungus in a proper environment are primary mycelia. When two compatible mycelia join together, each cell receives a nucleus from the other mycelium by cell walls lysis for undergoing mitosis. Growing with conjugated splitting, the formed mycelia having two nuclei are called "secondary mycelia" as used herein.

In the method of the present disclosure for culturing fruiting bodies of *Antrodia cinnamomea*, fruiting bodies of *Antrodia cinnamomea* can be yielded from a subculture or, alternatively, yielded from a solid culture or a liquid culture after the subculture.

Steps for a subculture include: inoculating *Antrodia cinnamomea* strains in a sterilized agar medium; performing subculturing to generate secondary mycelia, selecting secondary mycelia with no-mutation and no-toxicity during the subculture, and subjecting the secondary mycelia with no-mutation and no-toxicity to a further subculturing to generate the fruiting bodies.

Preparation of agar medium includes mixing Yeast Malt (YM) agar medium as a base with edible oil and yeast extract, allowing the agar medium to contain the edible oil in an amount greater than 0% and less than 1% based on the total weight of the sterilized agar medium, and the yeast extract in an amount greater than 3% and less than 5% based on the total weight of the sterilized agar medium. In addition, the aforementioned yeast extract can choose the commercially available product without specific limits.

Then, a solid agar medium is formed by placing a agar medium solution in a sterilizable container for a common sterilization program, for example, using a sterilization kettle conventionally used in laboratory microorganism culture, performing a moist heat sterilization process by high temperature saturated steam generated in a closed high pressure environment, pouring the agar medium solution after sterilization into at least one culture dish, and forming the agar medium in solid by leaving the agar medium solution standing and cooling. Thereafter, *Antrodia cinnamomea* strains are inoculated in the agar medium for a subculture. The inventor surprisingly found that by performing a subculture in a particular environment, *Antrodia cinnamomea* secondary mycelia can grow, and then granular fruiting bodies of *Antrodia cinnamomea* grow. Further, triterpenoids components in the fruiting bodies of *Antrodia cinnamomea* are very similar to those contained in *Antrodia cinnamomea* grown in the wild and/or with the basswood cultivation.

During a subculture, the secondary mycelia with no-mutation and no-toxicity are selected after at least a first subculture (including the first subculture) has been performed and are subjected to a further subculture to generate fruiting bodies of *Antrodia cinnamomea*.

During a subculture such as in a first subculture, secondary mycelia with no-mutation and no-toxicity can be selected and subjected to a further subculture to generate fruiting bodies of *Antrodia cinnamomea*.

In addition, in the method of the present disclosure for culturing fruiting bodies of *Antrodia cinnamomea*, the edible oil can be any edible oil and grease, such as vegetable oil, animal oil or edible essential oil, preferably *Antrodia cinnamomea* essential oil. Preferably, a content of the edible oil is 0.5% based on the total weight of the sterilized agar medium.

In one embodiment, the secondary mycelia with no-mutation and no-toxicity and the fruiting bodies are selected from the agar medium after a subculture has been performed in the agar medium to generate secondary mycelia with no-mutation and no-toxicity and fruiting bodies, and then the secondary mycelia with no-mutation and no-toxicity and the fruiting bodies are inoculated in a sterilized solid medium in a container to generate further subcultures of the secondary mycelia with no-mutation and no-toxicity or the fruiting bodies. In addition, secondary mycelia with no-mutation and no-toxicity and fruiting bodies generated in a different subculture can be harvested from the agar medium for hybridizing culture.

The aforementioned sterilized solid medium comprises a solid portion of at least one type of grains; and a liquid portion containing at least one of a saccharide, yeast extract and edible oil. In one embodiment, the solid portion comprises a plurality of types of grains, such as two types of grains, and each type of grains is contained in an amount of 40-60% based on the total weight of the solid portion. In non-limiting examples, the grains can be selected from black glutinous rice or oat.

In one embodiment, the solid portion comprises 40-60% of black glutinous rice and 40-60% of oat, preferably 50% of black glutinous rice and 50% of oat.

A choice of the saccharide is not limited, and the saccharide can be selected from monosaccharide or disaccharide. In one embodiment, the saccharide is at least one selected from the group consisting of glucose, mannose and fucose.

In the solid medium, based on the total weight of the liquid portion, the saccharide is in an amount of from 3% to 5%, the yeast extract is in an amount of from 3% to 5%, and the edible oil is in an amount greater than 0% and less than 1%, and a height of the liquid portion in the container is from semi-high of the solid portion to substantially equal-high as a top surface of the solid portion. In one embodiment, the liquid portion comprises 20% of yeast extract, 20% of glucose, 20% of mannose, 20% fucose, and 0.5% of *Antrodia cinnamomea* essential oil.

Prior to a solid culture, the solid medium can be placed in a sterilizable container and subjected to a common sterilization program, and then secondary mycelia with no-mutation and no-toxicity and fruiting bodies are selected from the agar medium and inoculated in the sterilized solid medium to further generate fruiting bodies. In general, the secondary mycelia with no-mutation and no-toxicity selected from the agar medium can generate secondary mycelia after a solid culture for 20 days to 1 month, and then a selection for mutation and toxicity is performed. Only the selected secondary mycelia with no-mutation and no-toxicity are further cultured for 1 to 3 months to generate fruiting bodies of *Antrodia cinnamomea*.

When the non-mutant and non-toxic fruiting bodies selected from the agar medium are cultured for 3 to 6 months, fruiting bodies of *Antrodia cinnamomea* can be generated.

In another embodiment, secondary mycelia with no-mutation and no-toxicity are harvested from the agar medium after subculture has been performed in the agar medium to generate secondary mycelia with no-mutation and no-toxicity, and then the secondary mycelia with no-mutation and no-toxicity are inoculated in a sterilized liquid medium in a container to generate fruiting bodies. The liquid medium comprises a saccharide, yeast extract and edible oil, wherein the saccharide is in an amount of from 3% to 5%, the yeast extract is in an amount of from 3% to 5%, and the edible oil is in an amount greater than 0% and less than 1% based on the total weight of the liquid medium.

In still another embodiment, the secondary mycelia with no-mutation and no-toxicity cultured in a solid medium are inoculated in a sterilized liquid medium in a container to generate fruiting bodies. The liquid medium comprises a saccharide, yeast extract, and edible oil, wherein the saccharide is in an amount of from 3% to 5%, the yeast extract is in an amount of from 3% to 5%, and the edible oil is in an amount greater than 0% and less than 1% based on the total weight of the liquid medium.

Steps for culturing fruiting bodies in the liquid medium in a container includes: stirring the sterilized liquid medium until an end stage of the culturing; stopping stirring the sterilized liquid medium, allowing the secondary mycelia with no-mutation and no-toxicity to float to a liquid level by increasing concentrations of the sterilized liquid medium and leaving the sterilized liquid medium standing to generate the fruiting bodies.

The end stage means the commonly known period over which a number of mycelia has no net increase with the growing time of mycelia. According to the method of the present disclosure, the end stage can be determined by detection during the culturing. In same embodiments, the end stage starts from 20 days to 1 month after beginning of the culturing. Additionally, various methods can be used to increase a concentration of a liquid medium. In one embodiment, the secondary mycelia with no-mutation and no-toxicity are allowed to float to a liquid level of the sterilized liquid medium by increasing concentrations of the yeast extract and saccharides, and the liquid medium is left standing to generate fruiting bodies. Additionally, in non-limiting examples, a concentration of liquid medium is enhanced by 5 folds, and fruiting bodies of *Antrodia cinnamomea* are generated by the culturing for 3 to 6 months.

Additionally, in one embodiment, the liquid medium comprises 4% of yeast extract, 4% of a saccharide and 0.5% of edible oil, preferably 4% of yeast extract, 4% of glucose and 0.5% of *Antrodia cinnamomea* essential oil. Since the *Antrodia cinnamomea* essential oil is contained in a low amount, it is possible to merely increase concentrations of the yeast extract and the saccharide when increasing a concentration of the sterilized liquid medium, for example, concentrations of the yeast extract and glucose can be increased to be 20% of yeast extract and 20% of glucose.

According to the method of the present disclosure, the particular environment indicates that a subculture is performed in an environment with relative humidity of 60%-70%.

In one embodiment, the particular environment indicates that the culturing is performed in an environment with relative humidity of 60%-70%, and at a culturing temperature maintained at 24° C.-27° C. for at least 10-14 hours per day, and at a culturing temperature maintained at 19° C.-23° C. for at least 10-14 hours per day.

In another embodiment, the particular environment indicates that the culturing is performed in an environment with relative humidity of 60%-70% at a culturing temperature maintained at 24° C.-27° C. for at least 10-14 hours per day, preferably, for sunshine hours such as daytime, and at a culturing temperature maintained at 19° C.-23° C. for non-sunshine hours such as nighttime.

In one embodiment, not limited to different geographical locations, a culturing temperature is maintained at 24° C.-27° C. for at least 10-14 hours for daytime from 6:00 to 18:00 with application of natural or artificial sunshine, particularly at least 90% of the temperature-maintained period is during daytime.

In one embodiment, not limited to different geographical locations, a culturing temperature is maintained at 19° C.-23° C. for at least 10-14 hours for nighttime from 18:00 to 6:00 without application of sunshine, particularly at least 90% of the temperature-maintained period is during nighttime.

In addition, in the method of the present disclosure for culturing fruiting bodies of *Antrodia cinnamomea*, selection for non-mutation and non-toxicity can be performed on *Antrodia cinnamomea* secondary mycelia and fruiting bodies of *Antrodia cinnamomea* in any step during the culturing.

EXAMPLES

Example 1: Subcultures

A solid agar medium was formed by following: using a Yeast Malt agar culture matrix (YM agar, purchased from Acumedia) as a base to mix with edible oil and yeast extract (purchased from Fengweitong) for a agar medium containing 0.5% of *Antrodia cinnamomea* essential oil and 4% of yeast extract (with water in balance); placing the mixed solution of agar medium in a sterilizable container; performing a sterilization program on the container and the agar medium solution therein in a sterilizing kettle; pouring the sterilized agar medium solution in a plurality of culture dishes; leaving the agar medium solution standing and cooling to form a solid agar medium.

*Antrodia cinnamomea* strains were inoculated in the solid agar medium, then the solid medium containing the *Antrodia cinnamomea* strains was placed in a particular environment to generate *Antrodia cinnamomea* secondary mycelia, wherein the particular environment include a temperature maintained at 24° C.-27° C. during daytime (from 6:00 to 18:00) and 19° C.-23° C. during nighttime (from 18:00 to 6:00) with relative humidity range of 60%-70%.

During the subculture, selection for mutation and toxicity was performed from the first subculture and only the selected secondary mycelia with no-mutation and no-toxicity were subjected to a further subculture, wherein for one generation of the subculture requires 20 days to 1 month. Finally, fruiting bodies were grown from the secondary mycelia with no-mutation and no-toxicity, and selection for mutation and toxicity was performed again when harvesting. FIG. 1 is a photograph showing fruiting bodies of *Antrodia cinnamomea* obtained from a subculture.

Example 2: Solid Cultures

Figure 2:
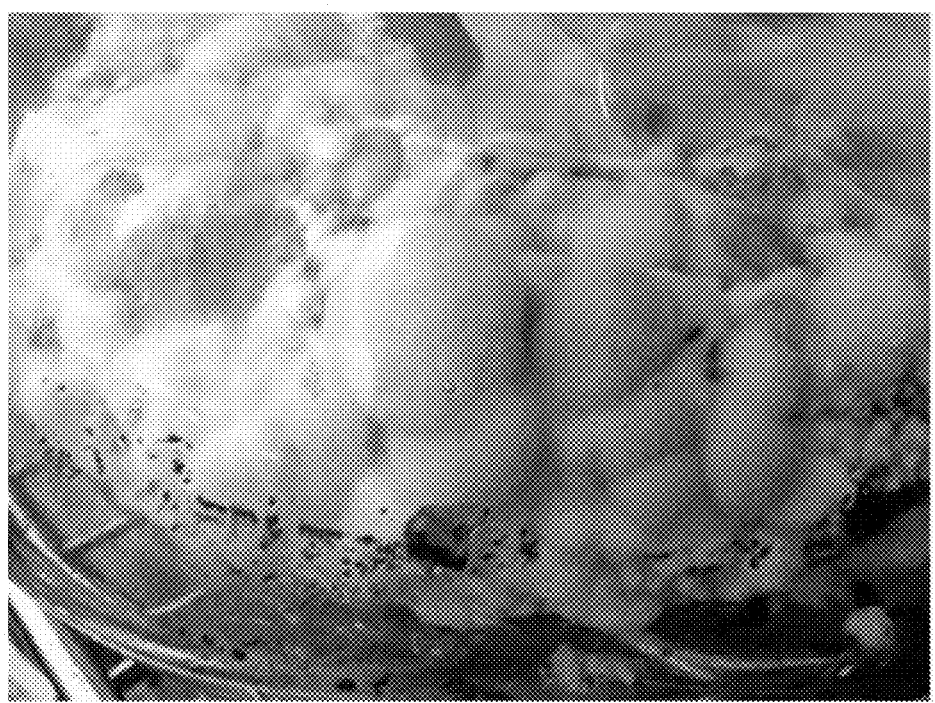
FIG. 2 is a photograph showing fruiting bodies of *Antrodia cinnamomea* obtained from a solid culture.

A solid medium was prepared in a sterilizable container, wherein the solid medium includes a solid portion and a liquid portion. The solid portion comprises 50% of black glutinous rice and 50% of oat; and the liquid portion comprises 20% of yeast extract, 20% of glucose, 20% of mannose, 20% of fucose and 0.5% of *Antrodia cinnamomea* essential oil, wherein a height of the liquid portion in the container is up to the same height of a top surface of the solid portion. A sterilization program was performed on the sterilizable container and the solid medium therein in a sterilizing kettle, and the secondary mycelia with no-mutation and no-toxicity from Example 1 was cultured in the solid medium. The solid medium was placed in an environment as described in Example 1 for the culturing for 20 days to 1 month to generate *Antrodia cinnamomea* secondary mycelia, and only the selected non-mutant and non-toxic *Antrodia cinnamomea* secondary mycelia was further cultured for 1 to 3 months to generate fruiting bodies of *Antrodia cinnamomea*. Finally, selection for mutation and toxicity was performed again when harvesting the fruiting bodies. FIG. 2 is a photograph showing fruiting bodies of *Antrodia cinnamomea* obtained from a solid culture.

Example 3: Solid Cultures

Figure 3:
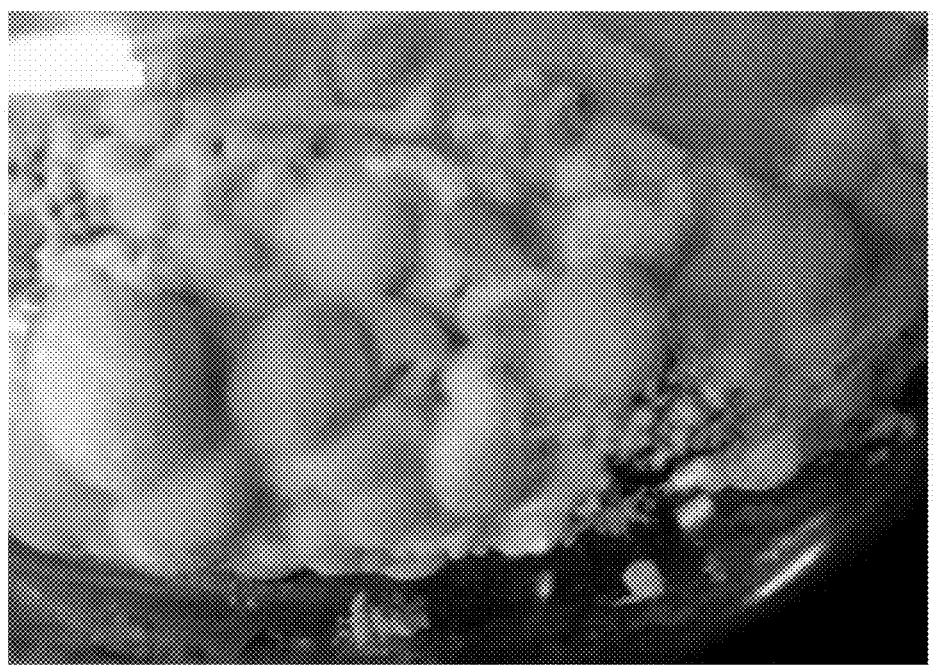
FIG. 3 is a photograph showing fruiting bodies of *Antrodia cinnamomea* obtained from a solid culture.

The non-mutant and non-toxic fruiting bodies selected in Example 1 were cultured in the solid medium with using the same solid medium and sterilization step as described in Example 2, and the culturing was performed in the solid medium in an environment as described in Example 1 for 3 to 6 months to generate fruiting bodies of *Antrodia cinnamomea*. Selection for mutation and toxicity is performed again when harvesting finally grown fruiting bodies. FIG. 3 is a photograph showing fruiting bodies of *Antrodia cinnamomea* obtained from a solid culture.

Example 4: Liquid Cultures

Figure 4:
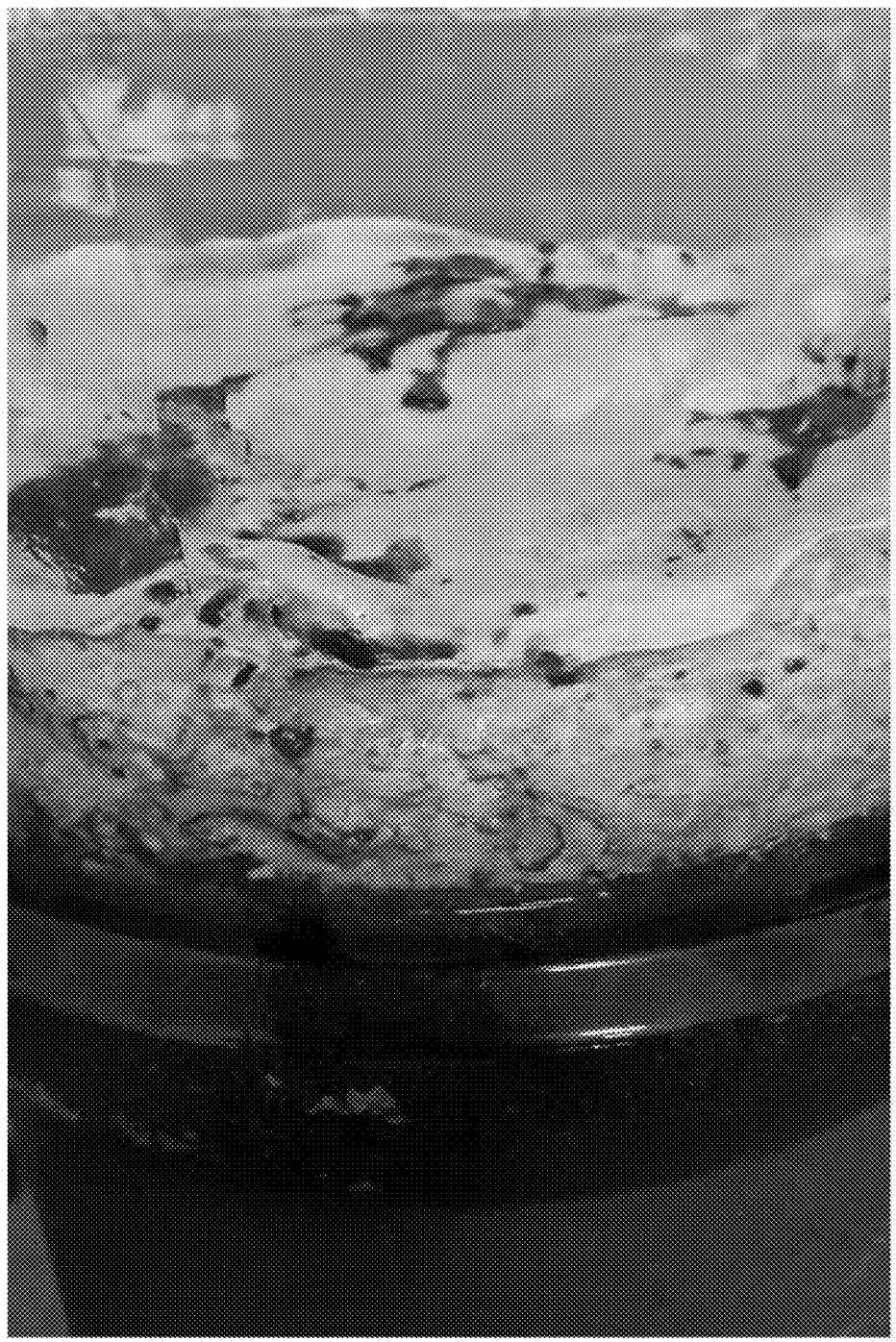
FIG. 4 is a photograph showing fruiting bodies of *Antrodia cinnamomea* obtained from a liquid culture.

A liquid medium comprising 4% of yeast extract, 4% of glucose and 0.5% of *Antrodia cinnamomea* essential oil was prepared and placed in a sterilizable container, and then the sterilizable container and contents therein were subjected to a sterilization program using a sterilizing kettle. The secondary mycelia with no-mutation and no-toxicity harvested from Example 1 were cultured in the liquid medium while stirring, the culturing was performed in the sterilized liquid medium in an environment as described in Example 1 while stirring until the culturing came to an end stage (for 20 days to 1 month). After stop stirring, a concentration of the sterilized liquid medium was increased by 5 folds (i.e., a concentration of the yeast extract is increased to 20%, a concentration of glucose was increased to 20%, and a concentration of the *Antrodia cinnamomea* essential oil was maintained intact). At the time, the secondary mycelia with no-mutation and no-toxicity were allowed to float to a liquid level due to the increased liquid concentration, the culturing was further performed for 3 to 6 months to generate fruiting bodies of *Antrodia cinnamomea*. Selection for mutation and toxicity is performed again when harvesting finally grown fruiting bodies. FIG. 4 is a photograph showing fruiting bodies of *Antrodia cinnamomea* obtained from a liquid culture.

Test Example 1: Tests for Types and Contents of Triterpenoids

In order to determine that the fruiting bodies of *Antrodia cinnamomea* obtained from the method of the present disclosure do comprise triterpenoids of functional ingredients, the HPLC chromatogram is used for comparison of a commercially available standard fruiting bodies of *Antrodia cinnamomea* (a), fruiting bodies of 5.5 year-old *Antrodia cinnamomea* grown in the wild and/or with the basswood cultivation (b), fruiting bodies of *Antrodia cinnamomea* obtained from a solid culture in Example 2 of the present application (c), fruiting bodies of *Antrodia cinnamomea* obtained from a solid culture in Example 3 of the present application (d), and fruiting bodies of *Antrodia cinnamomea* obtained from a liquid culture in Example 4 of the present application (e).

Extraction of Triterpenoids from Test Samples 50 mg of samples (a) to (e) was weighed and added into 5 mL of deionized water respectively, and then each solution was subjected to extraction for two times (for 3 hours per time) in a water bath at 80° C. Then the solutions were centrifuged to remove supernatant (containing water soluble substances), and solids at the lower layer were lyophilized and weighed. The dried substance was added into 50-fold volume of absolute ethanol (purchased from SIGMA with NO. 32221). The mixture was subjected to triterpenoids extraction for 1.5 hours, and centrifuged to collect supernatant (containing triterpenoids) repeatedly for three times. The obtained supernatant was lyophilized, and the dried products were dissolved in 10 mL of absolute ethanol to form aqueous solutions (a) to (e) respectively for analysis of triterpenoids types with an HPLC apparatus.

HPLC Analysis

Analysis and comparison were performed by respectively drawing 2 μL of aqueous solutions (a) to (e), and injecting them into an HPLC apparatus for HPLC analysis at a flow rate of 200 μL/min through a C18 column (2.1×100 mm, particle size of 3 μm) and at a detection wavelength of 244 nm.

Results of HPLC Analysis

Figure 5:
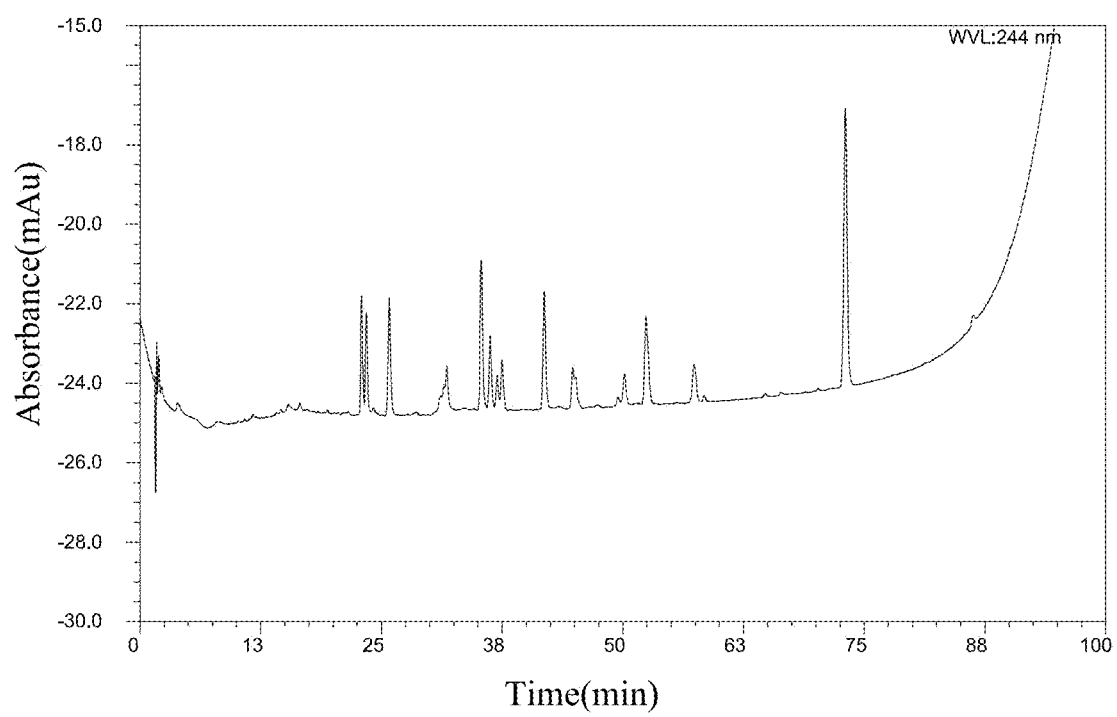
FIG. 5 is an HPLC chromatogram of commercially available standard of fruiting bodies of *Antrodia cinnamomea* (containing 11 standards).

Aqueous solution (a) of the commercially available standard fruiting bodies of *Antrodia cinnamomea*:

the commercially available standard of fruiting bodies of *Antrodia cinnamomea* comprises 11 standard components, as shown in FIG. 5, wherein retention time of components are (1) Antcin K, 22.94 and 23.43 mins, (2) Benzodioxole, 25.82 mins, (3) methyl antcinate K, 31.47 and 31.77 mins, (4) Antcin C, 35.34 and 36.27 mins, (5) Antcin H (Zhankuic acid C), 36.99 and 37.49 mins, (6) dehydrosulphurenic acid, 41.86 mins, (7) Antcin B, 44.82 and 45.10 mins, (8) eburicoic acid, 50.17 mins, (9) Antcin A, 52.41 mins, (10) methyl antcinate b, 57.40 mins, and (11) dehydroeburicoic acid, 73.05 mins, respectively.

Figure 6:
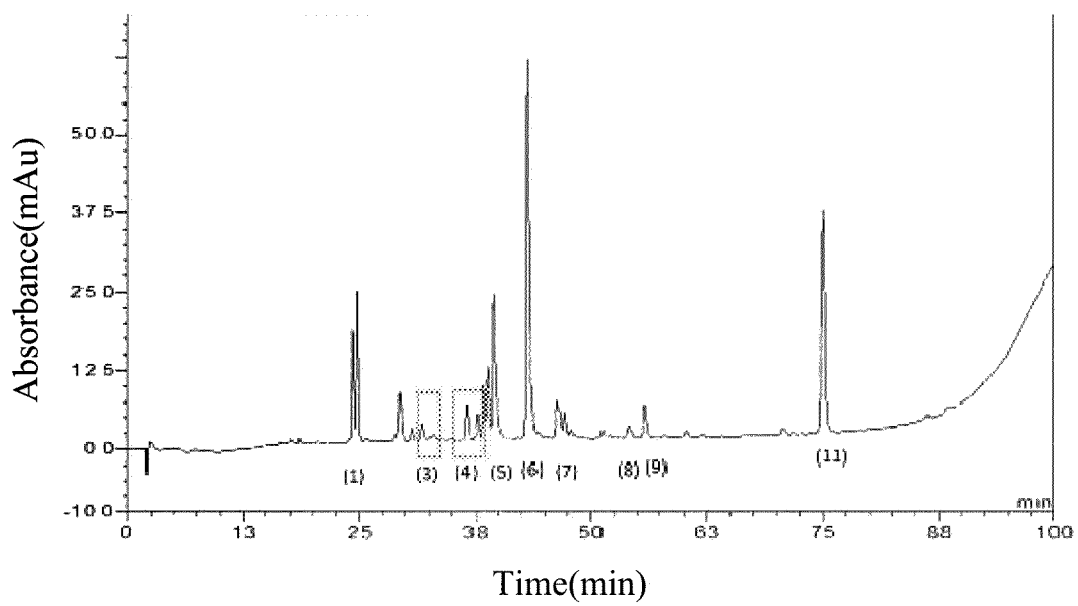
FIG. 6 is an HPLC chromatogram of 5.5 year-old fruiting bodies of *Antrodia cinnamomea* grown in the wild (and/or with the basswood cultivation).

Triterpenoids extract solution (b) extracted from the fruiting bodies of 5.5 year-old *Antrodia cinnamomea* grown in the wild (and/or with the basswood cultivation):

Compared with the commercially available standards, as shown in FIG. 6, triterpenoids contained in fruiting bodies of 5.5 year-old *Antrodia cinnamomea* grown in the wild (and/or with the basswood cultivation) includes following 9 types: (1) Antcin K, 24.15 and 24.65 mins, (3) Methyl antcinate K, 32.61 and 32.64 mins, (4) Antcin C, 36.67 and 37.62 mins, (5) Antcin H (Zhankuic acid C), 38.29 and 38.78 mins, (6) Dehydrosulphurenic acid, 43.17 mins, (7) Antcin B, 46.28 mins, (8) Eburicoic acid, 51.20 mins, (9) Antcin A, 54.03 mins, and (11) Dehydroeburicoic acid, 74.97 mins.

Percentages of types and contents of triterpenoids were compared. Calculation is performed by calculating area of each peak in the chromatogram and adding areas of each peak as a total content. Percentages of contents are obtained by dividing triterpenoids to be compared with areas of a total content. The calculated contents of triterpenoids are about: (1) 13.26%, (3) 1.32%, (4) 3.98%, (5) 11.94%, (6) 33.16%, (7) 4.14%, (8) 1.32%, (9) 2.65% and (11) 21.22%.

Figure 7:
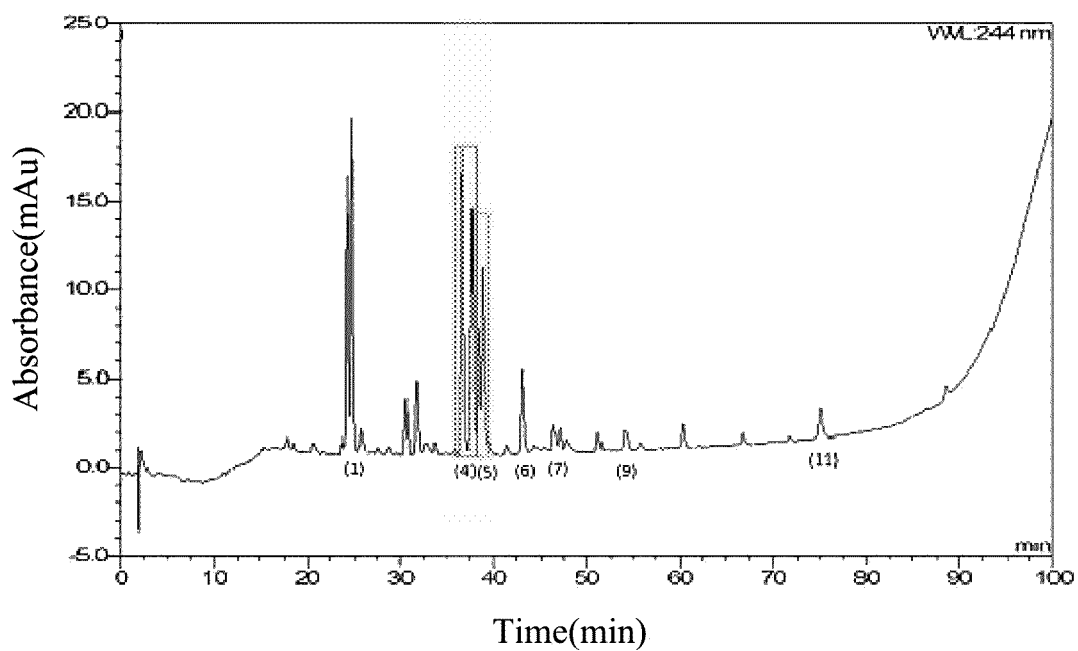
FIG. 7 is an HPLC chromatogram of fruiting bodies of *Antrodia cinnamomea* obtained from a solid culture in Example 2 of the present disclosure.

Triterpenoids extract solution (c) extracted from the fruiting bodies of *Antrodia cinnamomea* obtained from solid culture in Example 2 of the present application:

Compared with the commercially available standards, as shown in FIG. 7, triterpenoids contained in the fruiting bodies of *Antrodia cinnamomea* obtained from a solid culture in Example 3 of the present application includes the following 7 types: (1) Antcin K, 25.28 and 25.95 mins, (4) Antcin C, 36.83 and 38.01 mins, (5) Antcin H (Zhankuic acid C), 38.69 and 38.94 mins, (6) Dehydrosulphurenic acid, 43.35 mins, (7) Antcin B, 46.53 mins, (9) Antcin A, 54.18 mins, and (11) Dehydroeburicoic acid, 75.05 mins.

Percentages of the compared types and contents of triterpenoids were calculated as described above. The calculated contents of triterpenoids are about: (1) 27.62%, (4) 24.86%, (5) 15.19%, (6) 6.90%, (7) 5.52%, (9) 1.65% and (11) 2.76%.

Figure 8:
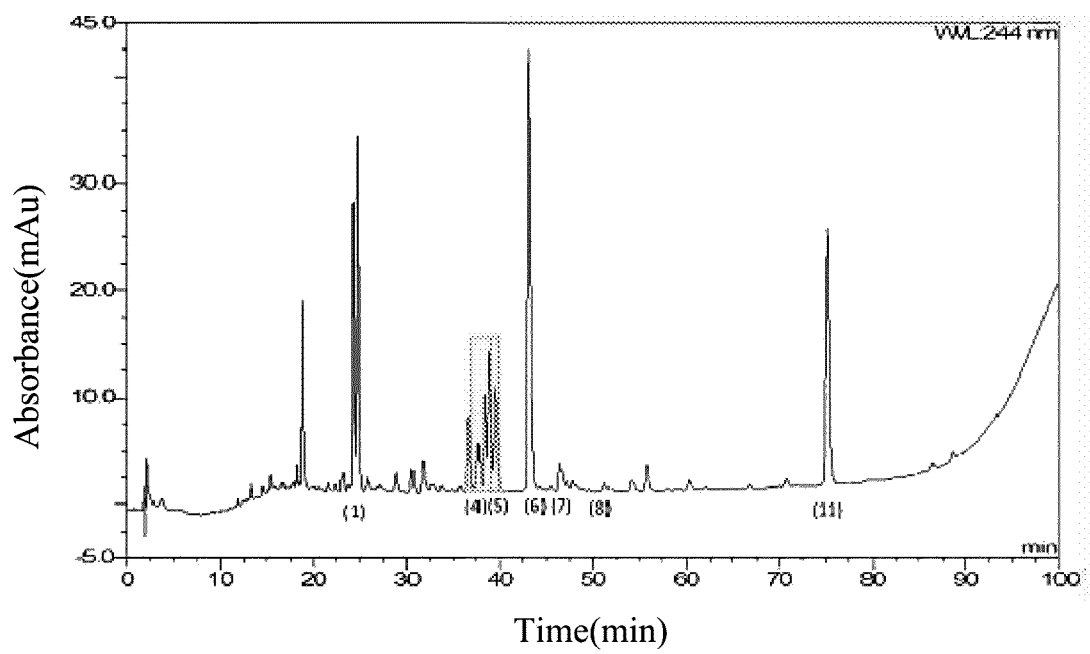
FIG. 8 is an HPLC chromatogram of fruiting bodies of *Antrodia cinnamomea* obtained from a solid culture in Example 3 of the present disclosure.

Triterpenoids extract solution (d) extracted from the fruiting bodies of *Antrodia cinnamomea* obtained from a solid culture in Example 3 of the present application:

Compared with the commercially available standards, as shown in FIG. 8, triterpenoids contained in the fruiting bodies of *Antrodia cinnamomea* obtained from a solid culture in Example 3 of the present application includes the following 7 types: (1) Antcin K, 24.533 and 25.179 mins, (2) Benzodioxole, 4.97 and 26.88 mins, (5) Antcin H (Zhankuic acid C), 39.57 and 40.06 mins, (6) Dehydrosulphurenic acid, 43.95 mins, (7) Antcin B, 47.21 mins, (8) Eburicoic acid, 51.58 mins, (10) Methyl antcinate b, 61.87 mins, and (11) Dehydroeburicoic acid, 75.42 mins.

Percentages of the compared types and contents of the triterpenoids were calculated as described above. The calculated contents of triterpenoids are about: (1) Antcin K 3.98%, (2) Benzodioxole 4.97%, (5) Antcin H, (Zhankuic acid C) 4.97%, (6) Dehydrosulphurenic acid 9.95%, (7) Antcin B 7.96%, (8) Eburicoic acid 5.97%, (10) Methyl antcinate b 1.99% and (11) Dehydroeburicoic acid 8.95%.

Figure 9:
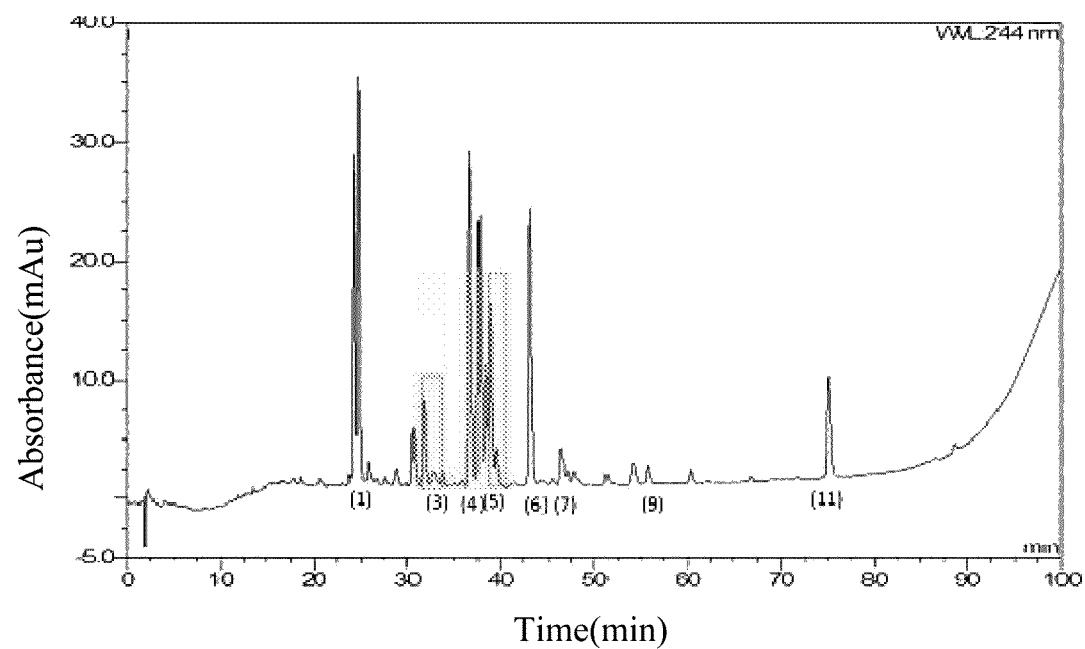
FIG. 9 is an HPLC chromatogram of fruiting bodies of *Antrodia cinnamomea* obtained from a liquid culture in Example 4 of the present disclosure.

Triterpenoids extract solution (e) extracted from the fruiting bodies of *Antrodia cinnamomea* obtained from liquid culture in Example 4 of the present application:

Compared with the commercially available standards, as shown in FIG. 9, triterpenoids in fruiting bodies of *Antrodia cinnamomea* obtained by a liquid culture in Example 4 of the present application includes the following 8 types: (1) Antcin K, 23.15 and 23.65 mins, (3) Methyl antcinate K, 34.51 and 34.78 mins, (4) Antcin C, 37.58 and 37.72 mins, (5) Antcin H (Zhankuic acid C), 39.14 and 39.52 mins, (6) Dehydrosulphurenic acid, 44.09 mins, (7) Antcin B, 47.32 mins, (9) Antcin A, 55.16 mins, and (11) Dehydroeburicoic acid, 75.85 mins.

Percentages of the compared types and contents of triterpenoids were calculated as described above. The calculated contents of triterpenoids are about: (1) 22.76%, (3) 5.20%, (4) 20.81%, (5) 11.38%, (6) 16.26%, (7) 1.62%, (9) 1.30% and (11) 6.50%.

By the culturing method provided in the present disclosure, fruiting bodies of *Antrodia cinnamomea* can be successfully grown in an aseptic environment, and by mimicking a growing environment of *Antrodia cinnamomea* grown in the wild and/or with the basswood cultivation, the most important components, triterpenoids, contained in fruiting bodies of *Antrodia cinnamomea* obtained from the present disclosure can be very similar to those in *Antrodia cinnamomea* grown in the wild and/or with the basswood cultivation, thereby bring about a health effect the same as the one of *Antrodia cinnamomea* grown in the wild and/or with the basswood cultivation.

The above examples are used to exemplarily illustrate, but not to limit the present disclosure in any way. The examples can be modified and altered by a person skilled in the art without departing from the spirit and scope of the present disclosure. Therefore, the modifications and alterations by a person skilled in the art without departing from the spirit and technical principle of the present disclosure should be encompassed by the accompanying claims.

What is claimed is:

1. A method for culturing fruiting bodies of *Antrodia cinnamomea*, comprising:
   inoculating *Antrodia cinnamomea* strains in a sterilized agar medium wherein the sterilized agar medium comprises a yeast malt (YM) agar culture matrix; edible oil in an amount greater than 0% and less than 1% based on a total weight of sterilized agar medium; and yeast extract in an amount greater than 3% and less than 5% based on the total weight of the sterilized agar medium;
   performing subculturing to generate secondary mycelia;
   selecting, during the subculturing, the secondary mycelia with no mutation and no toxicity;
   subjecting the selected secondary mycelia with no mutation and no toxicity to a further subculturing to generate subcultures of the secondary mycelia with no mutation and no toxicity or the fruiting bodies; and
   inoculating at least one of the secondary mycelia with no mutation and no toxicity and the fruiting bodies in a sterilized solid medium in a container to generate further subcultures of the secondary mycelia with no mutation and no toxicity or the fruiting bodies, wherein the sterilized solid medium comprises:
      a solid portion containing at least a type of grain; and
      a liquid portion containing at least one of a saccharide, yeast extract and edible oil,
      wherein a height of the liquid portion in the container is from substantially semi-high of the solid portion to substantially equal-high as a top surface of the solid portion.

2. The method of claim 1, wherein the edible oil is edible essential oil, *Antrodia cinnamomea* essential oil, vegetable oil or animal oil.

3. The method of claim 1, wherein the edible oil is in an amount of about 0.5% based on the total weight of the sterilized agar medium.

4. The method of claim 1, wherein, based on a total weight of the liquid portion, the saccharide is in an amount of from 3% to 5%, the yeast extract is in an amount of from 3% to 5%, and the edible oil is in an amount greater than 0% and less than 1%.

5. The method of claim 1, wherein the solid portion comprises two types of grains, and each type of the grains is in an amount of from 40% to 60% based on a total weight of the solid portion.

6. The method of claim 1, wherein the saccharide is at least one selected from the group consisting of glucose, mannose and fucose.

7. The method of claim 1, wherein the secondary mycelia with no mutation and no toxicity and the fruiting bodies to be inoculated are harvested from different subcultures in the sterilized agar medium.

8. The method of claim 1, further comprising inoculating the secondary mycelia with no mutation and no toxicity in the sterilized solid medium into a sterilized liquid medium in a container to generate the fruiting bodies.

9. The method of claim 8, wherein the sterilized liquid medium comprises at least one of a saccharide, yeast extract and edible oil, and wherein the saccharide is in an amount of from 3% to 5%, the yeast extract is in an amount of from 3% to 5%, and the edible oil is in an amount greater than 0% and less than 1% based on a total weight of the sterilized liquid medium.

10. The method of claim 1, wherein the subculturing is performed in an environment with relative humidity of from 60% to 70%.

11. The method of claim 1, wherein during the subculturing per day, a temperature of the subcultures is maintained at 24° C. to 27° C. for at least 10 to 14 hours and at 19° C. to 23° C. for at least 10 to 14 hours.

* * * * *